(12) United States Patent
Spencer et al.

(10) Patent No.: US 7,407,684 B2
(45) Date of Patent: Aug. 5, 2008

(54) MULTI-STEP METHOD OF MANUFACTURING A MEDICAL DEVICE

(75) Inventors: Steven M. Spencer, Minneapolis, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 382 days.

(21) Appl. No.: 10/765,065

(22) Filed: Jan. 28, 2004

(65) Prior Publication Data

US 2005/0163913 A1    Jul. 28, 2005

(51) Int. Cl.
*B05D 5/00* (2006.01)
(52) U.S. Cl. .............. 427/2.1; 427/2.24; 427/2.25; 427/2.26; 427/2.27; 427/2.28; 427/2.3; 427/8
(58) Field of Classification Search .......... 427/2.1, 427/2.24, 2.25, 2.26, 2.27, 2.28, 2.3, 8
See application file for complete search history.

(56) References Cited

U.S. PATENT DOCUMENTS

| | | | |
|---|---|---|---|
| 5,443,458 A | 8/1995 | Eury et al. | |
| 5,679,400 A * | 10/1997 | Tuch | 427/2.14 |
| 5,972,027 A | 10/1999 | Johnson et al. | |
| 6,179,817 B1 * | 1/2001 | Zhong | 604/265 |
| 6,368,658 B1 | 4/2002 | Schwarz et al. | |
| 6,702,850 B1 * | 3/2004 | Byun et al. | 623/1.44 |
| 6,783,793 B1 * | 8/2004 | Hossainy et al. | 427/2.25 |
| 6,928,338 B1 * | 8/2005 | Buchser et al. | 700/265 |
| 7,163,555 B2 * | 1/2007 | Dinh | 623/1.42 |
| 7,195,640 B2 * | 3/2007 | Falotico et al. | 623/1.42 |
| 2002/0051730 A1 | 5/2002 | Bodnar et al. | |
| 2002/0065553 A1 * | 5/2002 | Weber | 623/1.46 |
| 2002/0087123 A1 * | 7/2002 | Hossainy et al. | 604/198 |
| 2003/0135195 A1 | 7/2003 | Jimenz et al. | |
| 2003/0216699 A1 * | 11/2003 | Falotico | 604/265 |
| 2004/0220656 A1 * | 11/2004 | Epstein et al. | 623/1.15 |
| 2004/0253185 A1 * | 12/2004 | Herweck et al. | 424/10.2 |
| 2005/0070997 A1 * | 3/2005 | Thornton et al. | 623/1.46 |

FOREIGN PATENT DOCUMENTS

| WO | WO 2004/004926 A1 | 1/2004 |
|---|---|---|
| WO | WO 2004/037443 A | 5/2004 |

OTHER PUBLICATIONS

European Patent Office Communication dated Jan. 3, 2008.

* cited by examiner

*Primary Examiner*—Erma Cameron
(74) *Attorney, Agent, or Firm*—Kenyon & Kenyon LLP

(57) ABSTRACT

A multi-step method of manufacturing a medical device containing therapeutic agents that results in a lower maximum error in the amount of therapeutic agents actually disposed thereon and that allows for differential drug release kinetics along the length of the medical device.

16 Claims, 2 Drawing Sheets

MULTI-STEP METHOD OF MANUFACTURING A MEDICAL DEVICE

FIELD OF THE INVENTION

The present invention relates to a multi-step method of manufacturing a medical device containing therapeutic agents disposed thereon.

BACKGROUND OF THE INVENTION

Minimally invasive medical devices such as stents, grafts, and balloon catheters, are used for a number of medical purposes including the treatment of vascular disease, reinforcement of recently re-enlarged lumens, and the replacement of ruptured vessels. It is often beneficial to incorporate in such medical devices, therapeutic agents, which are often contained within a coating applied to the surface of the medical device, to provide desired therapeutic properties and effects. For example, it is useful to apply a coating containing therapeutic agents to medical devices to provide for the localized delivery of therapeutic agents to target locations within the body, such as an occluded body lumen. Compared to systemic drug administration, such localized drug delivery minimizes unwanted effects on parts of the body which are not to be treated and allows for the delivery of higher amounts of therapeutic agent to the afflicted part of the body. Coatings containing therapeutic agents may also provide for controlled release, which includes long-term or sustained release, of the therapeutic agent.

Conventionally, coatings have been applied to medical devices by processes such as dipping, spraying, vapor deposition, plasma polymerization, and electro-deposition. Although these processes have been used to produce satisfactory coatings, there are numerous drawbacks associated with these processes. For example, with current spraying processes, it is difficult to achieve a narrow weight distribution of the therapeutic agent on the medical device. Furthermore, the evaporation of solvents used in the coatings, the complex geometries of many medical devices, and the low amounts of therapeutic agents applied to the coatings contribute to the difficulty in measuring the amount of therapeutic agent actually disposed on the medical device. In addition, there is no direct feedback loop associated with these medical devices to ascertain the actual amount of therapeutic agent disposed on the medical device and therefore it is often necessary to maintain processing parameters as constant as possible. However, due to the large number of processing parameters associated with coating a medical device, there is still a significant amount of variation in the amount of drug disposed on the medical device.

In addition to the difficulties associated with achieving a narrow weight distribution of a therapeutic agent on a medical device, current coating procedures are designed to result in a uniform application of therapeutic agent across the medical device, which is suitable and often desired for many current medical devices. Such a coating process, however, does not allow for differentiation in drug amount across the medical device. Therefore, there is a need in the art for a coating process that allows for a broader weight distribution on the medical device and that allows for non-uniform application of the therapeutic agent on the medical device.

SUMMARY OF THE INVENTION

The present invention provides a method of manufacturing a medical device comprising a total desired amount of a first and second therapeutic agent disposed thereon. The method includes applying a first desired amount of a first therapeutic agent to a first portion of a medical device and then determining a first actual amount of the first therapeutic agent, wherein the first actual amount is the amount of the first therapeutic agent actually disposed on the first portion of the medical device. The method further comprises applying a second desired amount of a second therapeutic agent to a second portion of a medical device, wherein the second desired amount is determined by calculating the difference between the total desired amount and the first actual amount.

The present invention additionally provides a method of manufacturing a medical device comprising a desired amount of a positive therapeutic agent disposed thereon. The method comprises applying a desired amount of a positive therapeutic agent to the medical device and then determining the actual amount of the positive therapeutic agent. The actual amount is the amount of the positive therapeutic agent that is actually disposed on the medical device. The method then comprises determining if the actual amount of the positive therapeutic agent is greater than the desired amount of the positive therapeutic agent. If the actual amount of the positive therapeutic agent is greater than the desired amount of the positive therapeutic agent, the method further comprises applying to the medical device, a negative agent that has a neutralizing or opposing effect on the positive therapeutic agent.

DETAILED DESCRIPTION OF THE INVENTION

Figure 1:
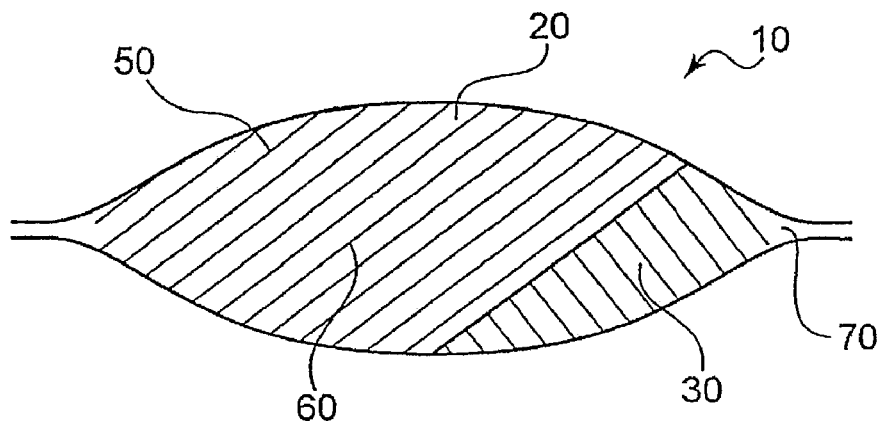
FIG. 1 illustrates a medical device according to an embodiment of the present invention.

As referred to herein, the terms "therapeutic agent" or "therapeutic agents" are used interchangeably with the term "drug" or "drugs." In addition, the use herein of the terms "first therapeutic agent" and "second therapeutic agent," does not necessarily mean the first and second therapeutic agents are different compositions although the first and second therapeutic agents may be different compositions. Similarly, the use herein of the terms "first coating" and "second coating" does not necessarily mean the first and second coatings are different compositions although the first and second coatings may be different compositions.

The present invention provides a multi-step method of manufacturing a medical device containing a first and a second therapeutic agent that results in a lower maximum error in the total amount of the first and the second therapeutic agent actually disposed on the medical device. In one embodiment, a method of manufacturing a medical device having a total desired amount of a first and a second therapeutic agent includes the steps of applying a first desired amount of a first therapeutic agent to a first portion of the medical device wherein the first desired amount refers to the predetermined amount of the first therapeutic agent desired to be applied to first portion of the medical device. The next step of the method of the present invention is determining a first actual amount of the first therapeutic agent. The first actual amount refers to the amount of the first therapeutic agent actually disposed on the medical device, which may be, and often is, different than the first desired amount of the first therapeutic agent applied to the first portion. After the first actual amount is determined, the method includes the step of applying a second desired amount of a second therapeutic agent to a second portion of the medical device, wherein the second desired amount is determined by calculating the difference between the total desired amount and the first actual amount. For example, if the total desired amount of a therapeutic agent desired to be applied to the medical device is 100 milligrams (mg) and the first portion comprises 40% of the surface area of the medical device, then a first desired amount of 40 mg of first therapeutic agent is applied to the first portion. The amount of first therapeutic agent actually disposed on the first portion is then measured by weighing, for example, the medical device. If the first actual amount of the first therapeutic agent disposed on the medical device is 36 mg, for example, then a second desired amount of 64 mg of the second therapeutic agent is applied to the second portion of the medical device. In a preferred embodiment, the first portion has a greater surface area than the second portion. In a more preferred embodiment, the first therapeutic agent is contained in a first coating that is applied to the first portion and the second therapeutic agent is contained in a second coating that is applied to the second portion.

The multi-step coating process according to the present invention provides for a lower maximum final error in the amount of the total first and second therapeutic agents disposed on the medical device. For example, with current industry standard processes of coating medical devices, there is approximately a +/−10% variation in the amount of therapeutic agent actually disposed on the medical device. If, for purposes of this example, the first portion comprises 90% of the medical device, then initially coating the first portion according to the present invention results in disposition of 81% to 99% of the total desired amount of the therapeutic agent. The amount of therapeutic agent subsequently applied to the second portion can thus be adjusted to between 1% and 19%, resulting in a maximum final error of disposed therapeutic agent being 2% instead of 10%.

Furthermore, because the first and second therapeutic agents are being applied to the medical device in separate steps, the medical device can have differential drug properties along its length. Specifically, first and second therapeutic agents can have differences in their drug release kinetics, such as difference in the amount, rate, and/or duration of drug release, which result in the medical device having differential drug release properties along its length. The specific differences in drug release kinetics can be targeted to the anatomical and/or pathological characteristics of the areas of the target site to which the first and second portions of the medical device (and therefore the first and second therapeutic agents) are respectively to be exposed. Non-limiting examples of such anatomical characteristics include the shape, diameter, number of side branches of the arteries, and location with respect to the ostium of the areas of the target site and the consequential flow behaviors of the areas of the target site. Non-limiting examples of pathological characteristics include the stage or presence of disease of the areas of the target site.

For example, if the area of the target site that is exposed to the first portion of the medical device is the "first area" and the area of the target site that is exposed to the second portion of the medical device is the "second area," the medical device may be placed in a bifurcation or ostium in a blood vessel and the first area may be an area of the blood vessel that experience greater turbulent flow (and therefore the first portion may have a greater exposure to deposited material in the vessel) than the second area of the target site. Similarly, the first area may be an outer arcuate section of a vessel and the second area may be an inner arcuate section of a vessel, such sections experiencing different flow behaviors. Furthermore, the medical device may be placed in a tapered vessel and the first area may have a greater diameter than the second area. Alternatively, the first area may be in a disease state and the second area may be in a non-diseased state. For example, the first area may be the site of a vulnerable plaque in an artery and the second area may be the unaffected side of the artery. Alternatively, the first area and the second area may both be diseased but the first area may be in a more advanced disease state than the second area of the target site. To account for these different anatomical and pathological characteristics of the first and second areas of the target site and therefore the different anatomical and pathological characteristics to which the first and second portions are exposed, the first and second therapeutic agents may have different drug release kinetics. With respect to these specific examples, first therapeutic agent would have an amount, duration and/or rate of release that is greater than that of second therapeutic agent. Of course, the above-mentioned anatomical and pathological characteristics are exemplary and merely illustrate examples of how and why the release kinetics of the first and second therapeutic agents may differ. The first and second portions of the medical device may be targeted to any anatomical and/or pathological conditions of the first and second areas of the target site.

Such differences in drug release kinetics of the first and second therapeutic agents can occur because of the different amounts of the first and second therapeutic agents that can be applied to the first and second portions, respectively, of the medical device during the multi-step manufacturing process. Furthermore, the compositions of the first and second therapeutic agents applied during the multi-step manufacturing process can be differed to provide for different drug release kinetics. For example, the first therapeutic agent may be a composition that has a sustained release rate and the second therapeutic agent may be a composition that has an immediate release rate. Alternatively, the compositions may have other different therapeutic properties dependent on the anatomical or pathological characteristics of the first and second areas. For example, in the case where the first area of the target site has a vulnerable plaque and the second area is non-inflamed, the first therapeutic agent may be an anti-inflammatory drug and the second therapeutic may be an endothelial cell stimulating substance.

Alternatively, the first and second therapeutic agents may be distributed in a first and a second coating respectively that are applied to the respective first portion and second portion of the medical device. The first and second coatings may have different properties such that the first and second therapeutic agents have different drug release kinetics. For example, the first and second coatings may be different polymer compositions that have different bioabsorption rates thereby providing different release rates of the first and second therapeutic agents. Alternatively, the first and second coatings may be manufactured of the same composition but may be applied to the first and section portions in different amounts such that the first and second coatings have different thickness, which also results in the first and second therapeutic agents having different release rates. Of course it is understood that these mechanisms of providing different drug release kinetics between the first and second therapeutic agents are merely exemplary and other mechanisms will be readily known to one in the art. Further, any described or known mechanism may be used alone or in combination with other mechanisms.

The first therapeutic agent and the second therapeutic agent used in the multi-step manufacturing process of the present invention comprise at least one first therapeutic agent and at least one second therapeutic agent. As such, the therapeutic agents should not be interpreted as necessarily being single respective therapeutic agents. The present invention contemplates the first therapeutic agent to include any number or combination of therapeutic agents and similarly contemplates the second therapeutic agent to include any number or combination of therapeutic agents.

Furthermore, although the aforementioned method of the present invention involves a two-step process, the application process may include more than two steps involving coating more than two portions of the medical device with more than two therapeutic agents. For example, to manufacture a medical device comprising a first portion, a second portion, and a third portion, therapeutic agents are sequentially applied to each portion with intermediate determinations of the actual amount of drug disposed on the medical device between application steps. Preferably the first, second and third portions have respectively decreasing surface areas. For example, if the total amount of therapeutic agent desired to be applied to the medical device is 100 milligrams (mg) and the first portion comprises 60% of the surface area, the second portion comprises 30% of the surface area, and the third portion comprises 10% of the surface area of the medical device, then a first desired amount of 60 mg of a first therapeutic agent is first applied to first portion. The amount of first therapeutic agent actually disposed on the first portion is then determined. If, for example, it is determined that 54 mg, for example, of the first therapeutic agent is actually disposed on the first portion, then in the next application step, a second desired amount of 36 mg of a second therapeutic agent is applied to the second portion. The amount of the second therapeutic agent actually disposed on the second portion is then measured. If, for example, it is determined that approximately 32 mg of the second therapeutic agent is actually disposed on the second portion, then in the next application step, approximately a third desired amount of 14 mg is applied to the third portion. Of course, the above-mentioned amounts are exemplary and merely illustrate an application of the multi-step application process according to the present invention.

In another embodiment, the multi-step coating process according to the present invention is performed before assembly of the medical device. In other words, the first portion and the second portion are initially separate and unconnected and coated with therapeutic agents while being separate and unconnected. After coating, the first and second portions are connected or otherwise attached to each other to form a fully assembled medical device. Specifically, in this embodiment, a first desired amount of a first therapeutic agent is applied to the first portion and a first actual amount of the first therapeutic agent is determined. Then a second desired amount of a second therapeutic agent is applied to the second portion by calculating the difference between the total desired amount and the first actual amount. The first and second portions are then assembled together.

With respect to how the first and second therapeutic agents are applied using the multi-step application process of the present invention, in embodiments where the first and second therapeutic agents are contained within first and second coatings respectively, the medical device may be sequentially coated by using a spraying process that involves covering the second portion, with a shield, for example, while coating the first portion and then covering the first portion while covering the second portion. Alternatively, the first and second portions may be coated using an inkjet coating principle by coating the first portion with a first therapeutic agent, which may be in the form of microdroplets and then coating the second portion with a second therapeutic agent, which may also be in the form of microdroplets. Alternatively, a single coating could be applied to the first and second portions of the medical device and then a first plurality of reservoirs and a second plurality of reservoirs could be created in the single coating, such as by a heat, UV, chemical, or laser source. In this embodiment, the part of the coating defining the first plurality of reservoirs coats the first portion and the part of the coating defining the second plurality of reservoirs coats the second portion. The first and second therapeutic agents could then be placed in the first and second plurality of reservoirs, respectively.

Figure 2:
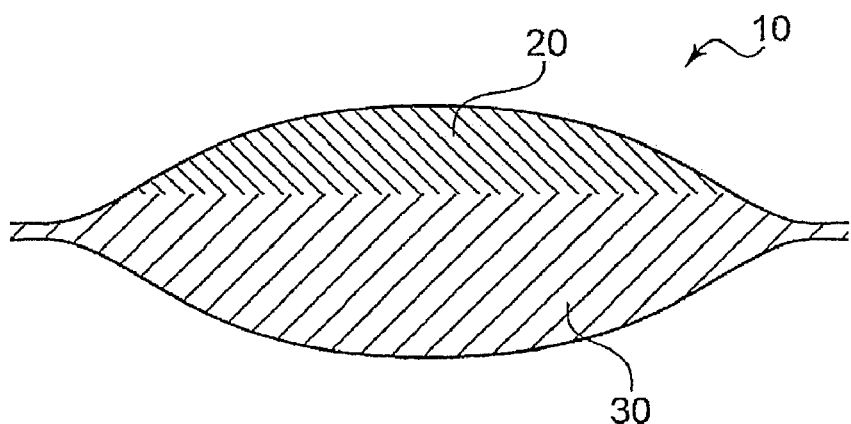
FIG. 2 illustrates a medical device according to an embodiment of the present invention.
Figure 3:
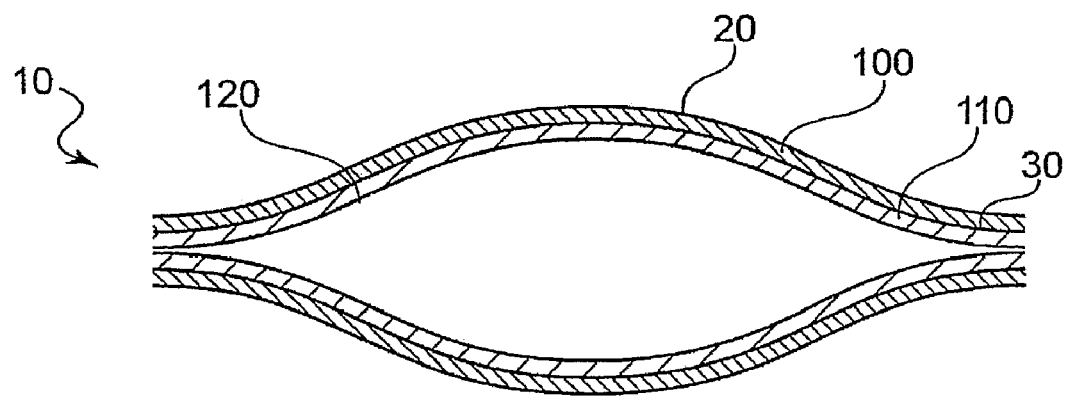
FIG. 3 illustrates a medical device according to an embodiment of the present invention.
Figure 4:
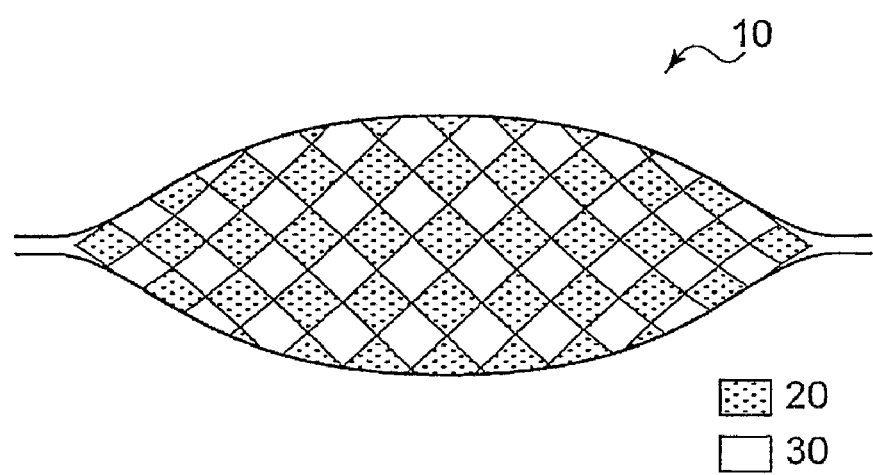
FIG. 4 illustrates a medical device according to an embodiment of the present invention.

With respect to the locations in which first and second therapeutic agents are applied to medical device, the first and second therapeutic agents may be applied to any relative locations of the medical device in any pattern or arrangement. For example, referring to FIG. 1, in embodiments where the first therapeutic agent is applied to first portion 20 and second therapeutic agent is applied to second portion 30 and first portion 20 has a greater surface area than second portion 30, a distal section 50 and a medial section 60 of medical device 10 may comprise first portion 20 and a proximal section 70 may comprise second portion 30. Accordingly, distal section 50 and medial section 60 would have a first therapeutic agent applied thereon, the amount of first therapeutic agent actually disposed on distal and medial sections 50 and 60 would be determined and then a second desired amount of a second therapeutic agent would be applied to proximal section 70, wherein the second amount is determined by calculating the difference between the total desired amount of therapeutic agent to be disposed on medical device 10 and the first actual amount of first therapeutic agent. Alternatively, referring to FIG. 2, first portion 20 and second portion 30 may be adjacent to each other with respect to the longitudinal axis of medical device 10. Referring to FIG. 3, in an alternative embodiment, first portion 20 comprises a first layer of coating 100 containing first therapeutic agent, and second portion 30 comprises a second layer of coating 110 containing a second therapeutic agent and located between first layer 100 and the outer surface 120 of medical device 10. Preferably, the locations where first and second therapeutic agents are applied to medical device 10 are targeted to the intended application of medical device 10 and in particular the anatomical or pathological characteristics of the target site to which first and second portions 20 and 30 are exposed. Referring to FIG. 4, in an alternative embodiment, first portion 20 and second portion 30 each comprise a plurality of subsections.

It should be emphasized that in the multi-coating process of the present invention, the medical device may comprise any number and/or pattern of portions and such portions may comprise any number and/or combination of therapeutic agents.

In another aspect, the present invention provides a multi-step coating process to manufacture a medical device comprising a total desired amount of a positive therapeutic agent. In this aspect, a negative agent that has a neutralizing or opposing effect on the positive therapeutic agent is applied to the medical device if, for example, an excess of the positive therapeutic agent is initially applied to the medical device. Specifically, the method comprises applying a desired amount of a positive therapeutic agent to the medical device and then determining the amount of the positive therapeutic agent actually disposed on the medical device (the actual amount). The method then comprises determining if the actual amount of the positive therapeutic agent is greater than the total desired amount of the positive therapeutic agent. If the actual amount of the positive therapeutic agent is greater than the total desired amount, i.e. an excess of positive therapeutic agent is actually disposed on the medical device, then a negative agent is applied to the medical device. In a more preferred embodiment, positive therapeutic agent and negative agent are each contained in coatings that are applied to the medical device. Negative agent can be any agent(s) that has a neutralizing or opposing effect on positive therapeutic agent. For example, negative therapeutic agent may be a solvent, a therapeutic agent, a source of energy, an agent that is activated by a source of energy, or electroactive polymers. In the case of negative agent being a therapeutic agent, combinations of positive therapeutic agent and negative agent include, for example, heparin and anti-heparin, and proteins and complementary neutralizing proteins. In the case of negative agent being a source of energy, negative agent could be ultraviolet light or heat that could be applied to medical device after application of positive therapeutic agent to de-activate positive therapeutic agent. In the case of negative agent being an agent that is activated by a source of energy, the desired amount of positive therapeutic agent could be encapsulated in microcapsules that are placed in a coating that is applied to the medical device. The microcapsules could also contain a negative agent such as paramagnetic particles that are activated upon application of an external magnetic field and that cause elimination of the coating upon activation. In such a circumstance, a magnetic field is exposed to areas of the medical device after the coating containing the microcapsules is applied to the medical device. Exposure to the magnetic energy activates the paramagnetic particles and causes degradation of the areas of the coating that are exposed to the magnetic energy thereby eliminating the positive therapeutic agent in those respective areas. Alternatively, the negative agent could be a conducting electro-active polymer (CEP), such as polypyrroles, polythiophenes, and polyanilines (I-III), which typically exhibit high electrical conductivity in the raneg 1-103 S cm−1. Such CEPs can be rapidly and reversibly switched between different oxidation states and can be synthesized by oxidative polymerization of the appropriate monomer. The oxidation can be achieved either chemically (e.g. using FeCl3 or S2O8 2— as an oxidant) or electrochemically in a conventional cell with the dopant anion (A−) being incorporated into the growing polymer chains.

As with other aspects of the present invention, the positive therapeutic agent and the negative agent comprise at least one positive therapeutic agent and at least one negative agent.

With respect to specific details of the present invention, therapeutic agents according to the present invention may be any pharmaceutically acceptable agents such as a non-genetic therapeutic agents, biomolecules, small molecules, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosporine, cis-platin, vinblastine, vincristine, epothilones, endostatin, trapidil, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

As mentioned above, the therapeutic agents may be incorporated into coatings and such coatings may comprise polymers that are biodegradable or non-biodegradable. Non-limiting examples of suitable non-biodegradable polymers include polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coatings may comprise multiple polymers and/or multiple therapeutic agents.

The coatings can be applied to the medical device by any known method in the art including dipping, spraying, rolling, brushing, electrostatic plating or spinning, vapor deposition, air spraying including atomized spray coating, and spray coating using an ultrasonic nozzle.

It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, and the like.

The medical devices of the present invention can be used, for example, in any application for treating, preventing, or otherwise affecting the course of a disease or tissue or organ dysfunction. For example, the methods and devices of the present invention can be used to induce or inhibit angiogenesis, as desired, to present or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

The foregoing description has been set forth merely to illustrate the invention is not intended as being limiting. Each of the disclosed embodiments may be considered individually or in combination with other embodiments of the invention, other variations, and other aspects of the invention. Modifications of the disclosed embodiments incorporating the spirit and substance of the invention may occur to persons skilled in the art. Therefore, the present invention should be construed to include everything within the scope of the appended claims and equivalents thereof.

We claim:

1. A method of manufacturing a medical device with an outer surface comprising a total desired amount of a first therapeutic agent and a second therapeutic agent disposed thereon:

applying a first desired amount of a first therapeutic agent to a first portion of the medical device;

determining a first actual amount of the first therapeutic agent, wherein the first actual amount is the amount of the first therapeutic agent disposed on the first portion of the medical device; and applying a second desired amount of a second therapeutic agent to a second portion of the medical device, wherein the second desired amount equals the difference between the total desired amount and the first actual amount, wherein the first portion and the second portion are at different locations on the outer surface of the medical device.

2. The method of claim 1, wherein the first portion has a greater surface area than the second portion.

3. The method of claim 1, wherein the first therapeutic agent is disposed in a first coating and the second therapeutic agent is disposed in a second coating.

4. The method of claim 3, wherein the first coating defines a first plurality of reservoirs and the second coating defines a second plurality of reservoirs, the first therapeutic agent being disposed in the first plurality of reservoirs and the second therapeutic agent being disposed in the second plurality of reservoirs.

5. The method of claim 1, wherein the first and the second therapeutic agents comprise different compositions.

6. The method of claim 1, wherein the first and the second therapeutic agents comprise the same compositions.

7. The method of claim 6, further comprising:
applying a desired amount of a different therapeutic agent that is a different composition than the first and second therapeutic agent to a third portion of the medical device;
determining an actual amount of the different therapeutic agent disposed on the third portion of the medical device; and
applying an additional desired amount of the different therapeutic agent on a fourth portion of the medical device, wherein the additional desired amount of the different therapeutic agent equals the difference between the total desired amount of the different therapeutic agent and the actual amount of the different therapeutic agent
wherein the third portion and the fourth portion are at different locations on the outer surface of the medical device.

8. The method of claim 1, wherein the first portion is exposable to a first area of a target site and the second portion is exposable to a second area of a target site, wherein the first and the second therapeutic agents have different release kinetics and wherein the different release kinetics are targeted to anatomical or pathological characteristics of the first area and the second area of the target site.

9. The method of claim 8, wherein the medical device further comprises a first coating in which the first therapeutic agent is disposed and a second coating in which the second therapeutic agent is disposed, wherein the different release kinetics are a result of the first and second coatings having different bioabsorption rates.

10. The method of claim 9, wherein the first and second coatings are different compositions.

11. The method of claim 8, wherein the target site is a blood vessel and the anatomical characteristics of the first area and the second area result in the first area experiencing greater turbulent flow than the second area.

12. The method of claim 8, wherein the pathological characteristics of the first area and the second area comprises the first area and the second area being in different stages of disease.

13. The method of claim 8, wherein the pathological characteristics of the first area and the second area comprises the first area being diseased and the second area being non-diseased.

14. The method of claim 1, wherein the first portion and the second portion are sequentially disposed along a longitudinal axis of the medical device.

15. The method of claim 1, wherein the first portion and the second portion are sequentially disposed along a transverse axis that is perpendicular to the longitudinal axis of the medical device.

16. The method of claim 1, wherein the first portion and the second portion are disposed in a checkerboard fashion over the outer surface of the medical device.

* * * * *

UNITED STATES PATENT AND TRADEMARK OFFICE
CERTIFICATE OF CORRECTION

PATENT NO. : 7,407,684 B2
APPLICATION NO. : 10/765065
DATED : August 5, 2008
INVENTOR(S) : Spencer et al.

It is certified that error appears in the above-identified patent and that said Letters Patent is hereby corrected as shown below:

Column 2, lines 62-63, "to first" should be changed to --to the first--;
Column 3, line 45, "difference" should be changed to --differences--;
Column 3, lines 65-66, "experience" should be changed to --experiences--;
Column 4, line 59, "section portions" should be changed to --second portions--;
Column 5, line 66, "while covering" should be changed to --while coating--;
Column 6, line 17, "medical device" should be changed to --the medical device--;
Column 7, line 19, "medical device" should be changed to --the medical device--;
Column 7, line 39, "raneg" should be changed to --range--;
Column 7, line 39, "S cm-1" should be changed to --S/cm--;
Column 7, line 43, "FeCl3 or S2O8 2-" should be changed to --$FeCl_3$ or $S_2O_8^{2-}$--;
Column 7, line 45, "(A-)" should be changed to --$A^-$--;
Column 7, lines 51-52, "a non-genetic therapeutic agents" should be changed to --non-genetic therapeutic agents--;
Column 7, line 63, "estrodiol" should be changed to --estradiol--;
Column 8, line 12, "lisidomine" should be changed to --linsidomine--;
Column 8, line 18, "Warafin" should be changed to --warfarin--;
Column 8, line 18, "Dicumarol" should be changed to --dicumarol--;
Column 8, line 20, "promotors" should be changed to --promoters--;
Column 8, lines 21-22, "promotors" should be changed to --promoters--;
Column 8, line 29, "endogeneus vascoactive" should be changed to --endogenous vasoactive--;
Column 8, line 43, "("MCP-1)" should be changed to --("MCP-1")--;
Column 8, line 44, ""("BMP's")" should be changed to --("BMPs")--;
Column 8, line 47, "BMPS" should be changed to --BMPs--;
Column 8, line 49, "homdimers" should be changed to --homodimers--;
Column 8, line 53, "the "hedghog" proteins" should be changed to --the "hedgehog" proteins--;
Column 8, line 53, "DNA's" should be changed to --DNAs--;
Column 9, line 2, "have" should be changed to --having--;

UNITED STATES PATENT AND TRADEMARK OFFICE
CERTIFICATE OF CORRECTION

PATENT NO. : 7,407,684 B2
APPLICATION NO. : 10/765065
DATED : August 5, 2008
INVENTOR(S) : Spencer et al.

It is certified that error appears in the above-identified patent and that said Letters Patent is hereby corrected as shown below:

Column 9, line 6, "allogenic" should be changed to --allogeneic--;
Column 9, line 7, "xenogenic" should be changed to --xenogeneic--;
Column 9, "(BAYHDROL®)" should be changed to --(BAYHYDROL®)--;
Column 9, line 32, "poly(D,L,-lactide)" should be changed to --poly(D,L-lactide)--; and
Column 9, line 33, "50/50 DL-lactide-co-glycolide)" should be changed to
--50/50 D,L-lactide-co-glycolide)--.

Signed and Sealed this

Eleventh Day of August, 2009

David J. Kappos
*Director of the United States Patent and Trademark Office*